United States Patent [19]

Beatty et al.

[11] Patent Number: 5,763,669
[45] Date of Patent: Jun. 9, 1998

[54] PROCESS FOR THE PREPARATION OF RUTHENIUM COMPLEXES AND THEIR IN SITU USE AS HYDROGENATION CATALYSTS

[75] Inventors: Richard Paul Beatty, Newark, Del.; Rocco Angelo Paciello, Durkheim, Germany

[73] Assignee: E. I. du Pont de Nemours and Company, Wilmington, Del.

[21] Appl. No.: 669,876

[22] Filed: Jun. 21, 1996

Related U.S. Application Data

[62] Division of Ser. No. 381,598, Jan. 31, 1995, Pat. No. 5,559,262.

[51] Int. Cl.⁶ .................................................. C07C 209/48
[52] U.S. Cl. ...................... 564/493; 564/491; 564/492; 560/155
[58] Field of Search ......................... 564/491, 493, 564/492; 560/155

[56] References Cited

U.S. PATENT DOCUMENTS

| | | | |
|---|---|---|---|
| 3,454,644 | 7/1969 | Dewhirst | 260/570.9 |
| 3,538,133 | 11/1970 | Knoth | 260/429 |
| 3,804,914 | 4/1974 | Fahey | 260/666 A |
| 3,957,827 | 5/1976 | Lyons | 260/343.3 R |
| 4,362,671 | 12/1982 | Diamond et al. | 260/465.5 R |
| 5,324,850 | 6/1994 | Juge et al. | 556/21 |
| 5,426,216 | 6/1995 | Genet et al. | 562/450 |
| 5,554,778 | 9/1996 | Beatty et al. | 556/21 |

OTHER PUBLICATIONS

Genet, J.P. et al, *Tet. Assym.*, 2, 43 (1991).
Chaudret, B. et al, *Organometallics*, 4, 1722 (1985).
Cooke, M. et al, *J. Chem. Soc.(A)*, p. 16 (1971).
Powell, J. et al, *J. Chem. Soc.(A)*, p. 159 (1968).
Chaudret, B. et al, *J. Am. Chem. Soc.* 113, 2314 (1991).
Christ, M.L. et al, *Organometallics*, 13, 3800–3804 (1994).
Armit, P.W. et al, *J. Chem. Soc., Dalton Transactions*, pp. 1663–1672 (1975).
Joshi, A.M. et al, *Inorg. Chim. Acta*, 198–200, 283–296 (1992).
Albers, M.O. et al, *Inorganic Syntheses*, 26, 68 (1989).
Joshi, A.M. et al, *Prog. in Catal.*, 73, 143 (1992).
Suarez, T. et al, *J. Mol. Cat.*, 45, 335 (1988).
Yoshida, T. et al, *J.C.S. Chem. Comm.*, 870 (1979).
Arliguie, T. et al, *Inorganic Chem.*, 27(4), 598 (1988).

*Primary Examiner*—Brian M. Burn

[57] ABSTRACT

This invention relates to a process of preparing a ruthenium complex of the formula $RuH_2(PR_3)_2L_2$ wherein $PR_3$ is an organophosphorus ligand and L is $H_2$ or $PR_3$; a catalyst comprising at least one ruthenium complex having the formula $RuH_2(PR_3)L^1_3$ wherein $L^1$ is a neutral electron pair donor ligand; a process for preparing the catalyst and its use in situ in the hydrogenation of nitriles.

15 Claims, No Drawings

PROCESS FOR THE PREPARATION OF RUTHENIUM COMPLEXES AND THEIR IN SITU USE AS HYDROGENATION CATALYSTS

This is a division of application Ser. No. 08/381,598, filed Jan. 31, 1995, now U.S. Pat. No. 5,559,262.

FIELD OF THE INVENTION

This invention provides a method of preparing ruthenium complexes from (COD)Ru(2-methyallyl)$_2$ type compounds and organophosphorous ligands in the presence of hydrogen. These complexes can be prepared and used in situ as catalysts in the hydrogenation of unsaturated substrates and are especially useful in the hydrogenation of nitriles.

TECHNICAL BACKGROUND

J. P. Genet, S. Mallart, C. Pinel, S. Juge, and J. A. Laffitte, Tet. Assym., 1991, vol. 2, p. 43, report reaction of (COD)Ru(2-methallyl)$_2$ with chiral bidentate phosphines to give Ru(P—P)(2-methylallyl)$_2$ complexes which, under hydrogen, catalyzed hydrogenation of olefins. The ruthenium complexes produced under hydrogen were not isolated or characterized.

B. Chaudret and R. Poilblanc, Organometallics, 1985, vol. 4, p. 1722, describe hydrogenation of the Ru(0) olefin complex, Ru(COD)(COT), in the presence of tricyclohexylphosphine to give RuH$_2$(H$_2$)$_2$(PCy$_3$)$_2$.

J. Powell and B. L. Shaw, J. Chem. Soc. (A), 1968, p. 159, describe the preparation of allylic complexes of ruthenium (II), Ru(all)$_2$(diolefin), where all=allyl or 2-methylallyl and diolefin=norbornadiene or 1,5-cyclooctadiene.

M. Cooke, R. J. Goodfellow, M. Green, and G. Parker, J. Chem. Soc.(A), 1971, p. 16 describe reaction of cyclooctadiene ruthenium bis(methylallyl) with phosphorus ligands to give (P ligand)$_2$Ru(2-methylallyl)$_2$.

W. H. Knoth, U.S. 3,538,133, describes preparation of RuH$_2$(Q$_2$)(PPh$_3$)$_3$, wherein Q is H or N, and some other closely related ruthenium complexes by reaction of RuHCl(PPh$_3$)$_3$ with triethylaluminum or sodium borohydride. However, the methods used to prepare the required RuHCl(PPh$_3$)$_3$ starting material are only applicable for closely related triarylphosphines, therefore the chemistry described by Knoth is not broadly applicable to a wide range of PR$_3$ ligands.

SUMMARY OF THE INVENTION

This invention provides a process for the in situ preparation of a ruthenium complex of formula I, RuH$_2$(PR$_3$)$_2$L$_2$, wherein

- each PR$_3$ is an organophosphorus ligand present as a separate ligand or cojoined with at least one other organophosphorus ligand;
- each R is a substituent independently selected from the group consisting of: H, R', OR', OSiR'$_3$, NH$_2$, NHR', and NR'$_2$;
- each R' is independently selected from the group consisting of: a hydrocarbyl group, and an assembly of at least two hydrocarbyl groups connected by ether or amine linkages;
- each L is a ligand selected from the group consisting of: H$_2$ and an additional equivalent of the organophosphorus ligand, PR$_3$; comprising contacting a ruthenium compound having the formula R$^2$$_2$RuA2 wherein R$^2$ is a mono- or poly-, cyclic or acyclic alkene ligand present as either two separate ligands or as a single polyalkene ligand and A is an allyl ligand or a hydrocarbyl-substituted allyl ligand, an organic solvent and PR$_3$ wherein the molar ratio of PR$_3$ to the ruthenium compounds is at least 2:1, with gaseous hydrogen; agitating the solution at a temperature of about −30° C. to about 200° C.; and optionally isolating the ruthenium complex from the organic solvent.

This invention also provides a catalyst, comprising at least one ruthenium complex of formula II

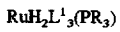

wherein:

- PR$_3$ is an organophosphorus ligand;
- each R is a substituent independently selected from the group consisting of: H, R', OR', OSiR'$_3$, NH$_2$, NHR' and NR'$_2$;
- each R' is independently selected from the group consisting of: a hydrocarbyl group, and an assembly of at least two hydrocarbyl groups connected by ether or amine linkages; and
- each L$^1$ is a neutral electron pair donor ligand selected from the group consisting of: H$_2$, N$_2$, nitriles, amines, alcohols, ethers, esters, amines, alkenes, alkynes, aldehydes, ketones and mines.

This invention also provides a process for the preparation of a catalyst comprising at least one ruthenium complex of formula II as described above, comprising contacting a ruthenium compound having the formula R$^2$$_2$RuA$_2$ as described above, an organic solvent, PR$_3$ wherein the molar ratio of PR$_3$ to the ruthenium compound ranges from 1 to <2 moles of PR$_3$ to 1 mole of the ruthenium compound, and at least one L$^1$ ligand, with gaseous hydrogen; and agitating the solution at a temperature of about −30° C. to about 200° C.

This invention further provides a process for the hydrogenation of an organic nitrile, comprising the steps of contacting the nitrile with gaseous hydrogen in the presence of a catalyst comprising at least one ruthenium complex of formula II, as described above; and subsequently agitating the nitrile, hydrogen and catalyst to form a primary amine. Preferred is the process wherein adiponitrile is reduced to 6-aminocapronitrile and/or hexamethylenediamine.

This invention further provides an in situ process for the hydrogenation of an organic nitrile comprising contacting the nitrile with a ruthenium compound having the formula R$^2$$_2$RuA$_2$ as described above, an organic solvent, PR$_3$ wherein the molar ratio of PR$_3$ to the ruthenium compound ranges from 1 to <2 moles of PR$_3$ to 1 mole of the ruthenium compound, and at least one L$^1$ ligand as described above for formula II, with gaseous hydrogen at a temperature from about −30° C. to about 200° C.; and subsequently agitating the solution to form a primary amine.

The invention provides a process for the selective hydrogenation of a dinitrile comprising contacting the dinitrile with gaseous hydrogen in the presence of a catalyst comprising at least one ruthenium complex of formula II and subsequently agitating the dinitrile, hydrogen and catalyst for an amount of time selected to favor yield of an aminonitrile over yield of a diamine.

The invention further provides an in situ process for the selective hydrogenation of a dinitrile comprising contacting the dinitrile with a ruthenium compound having the formula R$^2$$_2$RuA$_2$ as described above, an organic solvent, PR$_3$ wherein the molar ration of PR$_3$ to the ruthenium compound ranges from 1 to <2 moles of PR$_3$ to 1 mole of the ruthenium compound, and at least one $L^1$ ligand as described above for formula II, with gaseous hydrogen at a temperature from about −30° C. to about 200° C.; and subsequently agitating the solution for an amount fo time selected to favor yield of an aminonitrile over yield of a diamine.

DETAILED DESCRIPTION OF THE INVENTION

The ruthenium complexes of formula I and formula II are useful as catalysts in rapidly hydrogenating substrates, such as alkenes, which are typically easy to hydrogenate. However, their main value lies in their ability to hydrogenate nitrile groups. Which are generally regarded as very difficult to hydrogenate. With dinitriles, the catalysts allow production of the intermediate aminonitriles with high selectivity.

Starting material for processes of the present invention for preparing ruthenium complexes of formula I or the catalyst comprising at least one ruthenium complex of formula II comprises ruthenium compounds having the formula $R^2{}_2RuA_2$, wherein $R^2$ represents an alkene ligand and A represents an allyl ligand or hydrocarbyl-substituted allyl ligand. The alkene ligands are straight chain, branched, or cyclic arrangements of carbon atoms connected by single, double, or triple carbon-to-carbon bonds, comprising at least one carbon-to-carbon double bond, and substituted accordingly with hydrogen atoms. The alkene ligands can be present either as two separate ligands or as a single polyalkene ligand. Polyalkene ligands such as cycloheptatriene, norbornadiene, and 1,5-cyclooctadiene (COD) are preferred, with 1,5-cyclooctadiene being the most preferred.

The ruthenium compound, $R^2{}_2RuA_2$, can be prepared by reaction of $R^2{}_2RuX_2$, wherein the alkene ligand is as described above and X represents halide or pseudohalogen (e.g., the anion of a protonic acid salt, such as nitrate or acetate), with an appropriate Grignard reagent, for example, 2-methylallyl magnesium chloride or allyl magnesium chloride, as described in Powell and Shaw, J. Chem. Soc. (A), 1968, 159. Such Grignard reagents are commonly prepared by reaction of the corresponding allylic halide with magnesium metal. Since there are a very large number of allylic halides known and possible, a very wide variety of A ligands can be considered, but since simple, inexpensive A ligands function as well as more complex A ligands, the choice of A ligand will ultimately be determined by cost and availability. Examples of preferred A ligands comprise allyl, 1-methylallyl, and 2-methylallyl, with 2-methylallyl being the most preferred.

In formula I and formula II, $PR_3$ represents an organophosphorous ligand, where each R is a substituent independently selected from the group consisting of H, R', OR', OSiR'$_3$, NH$_2$, NHR', and NR'$_2$ where each R' is a hydrocarbyl group or an assembly of at least two hydrocarbyl groups connected by ether or amine linkages. Organophosphorus ligands comprise phosphines phosphinites, phosphonites and phosphites. By hydrocarbyl group is meant a straight-chain, branched, or cyclic arrangement of carbon atoms connected by single, double, of triple carbon-to-carbon bonds and substituted accordingly with hydrogen atoms. Such hydrocarbyl groups can be aromatic and/or aliphatic, for example, phenyl, aryl, alky, cycloalkyl, alkenyl, cycloalkenyl, alknyl, and aralkyl. Assemblies of at least two hydrocarbyl groups connected by ether or amine linkages comprise alkoxy, arlyoxy, pyridyl and aminoalkyl groups. Suitable hydrocarbyl groups or assemblies of hydrocarbyl groups comprise methyl, ethyl, propyl, isopropyl, butyl, isobutyl, tert-butyl, cyclopropyl, cyclobutyl, cyclopentyl, methylcyclopentyl, cyclohexyl, methylcyclohexyl, benzyl, phenyl, napthyl, o-tolyl, m-tolyl, p-tolyl, xylyl, vinyl, allyl, butenyl, cyclohexenyl and cyclooctenyl. β-methoxyethyl, 4-methoxybutyl, 2-pyridyl, 4-(N,N-diethylamino)butyl and 2-methoxy phenyl.

Representative examples of organophosphorus $PR_3$ ligands comprise cyclohexylphosphine, phenylphosphine, diethylphosphine, dicyclohexylphosphine, diphenylphosphine, trinethylphosphine, triethylphosphine, tri-n-propylphosphine, tri-isopropylphosphine, tri-n-butylphosphine, tri-isobutylphoshine, tri-t-butyl-phosphine, triphenylphosphine, tricyclohexylphosphine, tribenzylphosphine, tris(2-pyridyl)phosphine, tri-p-tolylphosphine, tris(p-trifluoromethylphenyl)-phosphine, o-diphenylphosphino-N,N-dimethylaniline, (3-N,N-diethylamino-propyl) di-isopropylphosphine, (4-N,N-dimethylaminobutyl)di-isopropylphosphine, diphenylmethylphosphine, dimethylphenylphosphine, dicyclohexyl(β-methoxy-ethyl) phosphine, and bis(β-methoxyethyl)phenylphosphine.

Other representative examples of $PR_3$ ligands comprise cyclohexyl-phosphite, phenylphosphite, diethylphosphite, cyclohexylphosphite, diphenylphosphite, dicyclohexylphosphite, diphenylphosphite, trimiethylphosphite, triethylphosphite, tri-n-propylphosphite, tri-isopropylphosphite, tri-n-butylphosphite, tri-isobutylphoshite, tri-t-butylphosphite, triphenylphosphite, tricyclohexylphosphite, tribenzylphosphite, tris(2-pyridyl)-phosphite, tri-p-tolylphosphite, tris(p-trifluoromethylphenyl)phosphite, tris (trimethylsilyl)phosphite, methyl diphenylphosphinite, ethyl diphenyl-phosphinite, isopropyl diphenylphosphinite, phenyl diphenylphosphinite, diphenyl phenylphosphonite, dimethyl phenylphosphonite, diethyl methylphosphonite, and diisopropyl phenylphosphonite.

Two or more $PR_3$ organophosphorus ligands can be cojoined, forming diphosphorus, triphosphorus, or polyphosphorus ligands. Examples of such diphosphine ligands comprise 1,2-bis(dimethylphosphino)ethane, 1,2-bis (diethyl-phosphino) ethane, 1,2-bis(dicyclohexylphosphin) methane, 1,2-bis[(β-methoxyethyl)phosphino]ethane, 1,2-bis-(diphenylphosphino) ethane, 1,3-bis(diphenylphosphino) propane, 1,4-bis(diphenyl-phosphino) butane, 1,2-bis (diphenylphosphino)benzene, (-)-1,2-bis((2R,5R)-2,5-dimethylphospholano) benzene, (R)-(+)-2,2'-bis (diphenylphosphino)1,1-binapthyl, bis(2-diphenylphosphinoethyl)phenylphosphine, tris(2-diphenylphosphinoethyl)-phosphine, and 1,1,1-tris (diphenylphosphinomethyl)ethane.

Diphosphites, diphosphinites, such as bis (diphenylphosphinito)2,2'-1,1-binaphthyl, and diphosphonites can also be employed as $PR_3$ ligand.

$PR_3$ ligands can also be attached to various polymer supports. Commercially available examples comprise the triphenylphosphine-on-styrene-divinylbenzene copolymers sold by Strem Chemicals and Aldrich Chemical Co. and the triorganophosphine-functionalized polysiloxanes (Deloxan® sol by Degussa AG, Hanau, Germany). Many other similar appropriate supports are known or can be readily prepared by methods known to those skilled in the art.

Larger electron-donating, trialkyl phosphines such as triisopropyl or tricyclohexyl phosphine are preferred, since they tend to give more catalytically active ruthenium complexes.

Ruthenium complexes of formula I can be prepared by contacting the ruthenium compound having the formula $R^2{}_2RuA_2$, as described above, the desired organophosphorus ligand $PR_3$, wherein the molar ratio of $PR_3$ to the ruthenium compound is at least 2:1 and an organic solvent with gaseous hydrogen. The solution is agitated, heated, and then the ruthenium complex is optionally isolated from the organic solvent.

Solvents which are usable in preparation of ruthenium complexes according to the present invention must be inert toward hydrogenation under the reaction conditions, must be liquid under the reaction conditions employed, and must be capable of dissolving sufficient ruthenium starting materail and hydrogen to form the desired ruthenium complex.

Although the solvent employed is normally and preferably anhydrous, this is not a strict requirement. While the amount of water present is normally, and preferably, less than about 0.01 mole of water per mole of nitrile, larger amounts of water, up to about 0.1 to about 1 mole of water per mole of nitrile, generally do not produce significant amounts of alcohol by-products. In the case of a hydrophobic nitrile and hydrophobic solvent, large amounts of water, even a second liquid phase, can be present and do not interfere with normal hydrogenation. Suitable solvents comprise $C_6$–$C_{12}$ non-fused benzenoid hydrocarbons and $C_1$–$C_{18}$ alkyl derivatives thereof, $C_5$–$C_{30}$ linear or branched saturated aliphatic or alicyclic hydrocarbons, $C_2$–$C_{12}$ aliphatic ethers, $C_4$–$C_{12}$ saturated aliphatic cyclic mono- or diethers, or $C_7$–$C_{14}$ aromatic ethers, or mixtures thereof. By the term "non-fused benzenoid hydrocarbons" is meant that if more than one benzene ring is present in the hydrocarbon, the rings are isolated and not fused together. Thus, the term encompasses biphenyl, but not naphthalene.

Suitable solvents further comprise the amines, especially those amines produced by hydrogenation of the above nitriles which are liquid at reaction temperature. Representative examples of specific useful solvents are ammonia, methylamine, ethylamine, n-propylamine, isopropylamine, n-butylamine, amylamine, azacycloheptane, 2-methyl-pentamethylenediamine and hexa-methyienediamine, xylene, hexamethylbenzene, biphenyl, n-octadecylbenzene, benzene, toluene, pentane, cyclopentane, cyclohexane, methylcyclohexane, hexane, isooctane, decane, cycodecane, tetrahydrofuran, p-dioxane, 2,5-dimethyltetrahydrofuran, methyl tetrahydrofurfuryl ether, dimethyl ether, 1,2-dimethoxyethane, diglyme, diethyl ether, diisopropyl ether, anisole, diphenylether, and mixtures thereof.

Preferred solvents comprise ammonia, THF, t-butyl methyl ether, toluene, n-amylamine, n-butylamine, 2-methyl-pentamethylenediamine, and hexamethylene-diamine. Most preferred, when the amine product of the hydrogenation is a liquid at reaction temperature, is to use that same amine product as the reaction solvent. For example, butylamine can be used as the solvent when hydrogenating butyronitrile or hexamethylenediamine can be used as the solvent when hydrogenating adiponitrile.

The source of hydrogen comprises hydrogen gas or a mixture of hydrogen gas with inert gases such as $N_2$, He, Ne, or Ar. Pure gaseous hydrogen is preferred. Mixtures comprising carbon monoxide, such as "synthesis gas" are not acceptable, since CO reacts with the desired ruthenium complex to form a carbonyl complex.

The partial pressure of hydrogen should be between about 100 kPa and about 15000 kPa. The preferred pressure is from about 700 kPa to about 7000 kPa. Higher pressures can be used, but are not required and generally do not justify the expense of the more exotic equipment required.

Because of the biphasic medium, effective agitation is required in order to provide sufficient contact of the gaseous hydrogen with the liquid phase for the hydrogenation reaction to occur.

The temperature employed can be from about –30° C. to about 200° C. The preferred range is from about 20° C. to about 100° C. If desired, the ruthenium complex can be isolated by one of a variety of methods, such as evaporation of solvent, crysallization by cooling, or precipitation by addition of a second organic solvent which is a poor solvent for the ruthenium complex. The exact isolation procedure depends on the amount and nature of the organic solvent used in the preparation. It is desirable to maintain a hydrogen atmosphere as much as possible during manipulation and isolation of the ruthenium complex to avoid loss of hydrogen from the ruthenium complex.

The process of the present invention is applicable to the preparation of ruthenium complexes having a very broad range of ligands. It provides for preparation of three classes of ruthenium complexes as shown below with their generic formula Class I: $RuH_2(PR_3)_4$ Class II: $RuH_2L(PR_3)_3$ Class III: $RuH_2L_2(PR_3)_2$ as well as a new class of ruthenium complex, $RuH_2L^1{}_3$ $(PR_3)$, Class IV. L, $L^1$ and R are as defined above for formula I. Some compounds of Classes I and II are quite well known, but complexes of Class III are rare.

Dihydrogen ligands present in certain ruthenium complexes of formula I can be displaced by dinitrogen ligands. In complexes where an L is $H_2$, either one or all such L can be displaced by dinitrogen, forming for example $RuH_2(H_2)$ $(N_2)(PR_3)_2$ or $RuH_2(N_2)_2(PR_3)_2$, hereafter referred to as "dinitrogen complexes." For example, sparging a solution of $RuH_2(H_2)_2(PCy_3)_2$ with nitrogen gas, thereby removing hydrogen from solution, results in rapid and quantitative conversion into $RuH_2(N_2)_2(PCy_3)_2$. This stable bis (dinitrogen) complex, which represents a completely new class of ruthenium complexes, was isolated and unambiguously characterized by x-ray crystallography. It contains two cis-hydride ligands, two cis- dinitrogen ligands, and two trans-tricyclohexylphosphine ligands arranged octahedrally around ruthenium.

Dinitrogen complexes are often more stable than dihydrogen complexes, for example, when catalyst is placed under a protective nitrogen atmosphere during storage, during preparation of feeds for a reaction, or during product separation or catalyst recycle.

Solvents which are useful in preparation of the dinitrogen complexes of the present invention should not themselves be capable of displacing L ligands to form complexes incorporating the solvent. Suitable solvents for preparation of dinitrogen complexes are hydrocarbons, comprising $C_6$–$C_{12}$ non-fused benzenoid hydrocarbons and $C_1$–$C_{18}$ alkyl derivatives thereof and $C_1$–$C_{30}$ linear or branched saturated aliphadc or alicyclic hydrocarbons. Mixtures of hydrocarbons can also be used, such as "petroleum ether," typically characterized by boiling range. By the term non-fused benzenoid hyrocarbons is meant that if more than one benzene ring is present in the hydrocarbon, the rings are isolated, not fused together. Thus, the term encompasses biphenyl but not naphthalene. Especially preferred solvents comprise toluene, pentane, hexane, and petroleum ether with a boiling range of about 35° to about 60° C.

Agitation is required to ensure adequate gas-liquid mass transfer, including both dissolution of dinitrogen gas into the reaction solution and loss of dihydrogen from the solution, and can be provided by any convenient method, such as stirring or gas sparging.

The temperature employed for this reaction is normally between about –80° C. and about 100° C. The preferred temperature is from about 15° C. to about 30° C. Higher temperatures increase reaction rate but adversely affect stability of the ruthenium complexes.

Pressure is not an important variable; normal atmospheric pressure is preferred, though higher or lower pressure can be employed if desired.

The reaction time required is determined mainly by the efficiency of gas contacting and removal of dihydrogen from the reaction mixture. With temperatures below about 30° C., reaction time is not critical; reaction times longer than the minimum essential time can be employed since the dinitrogen complexes are stable at those temperatures. With reaction temperatures above about 30°–40° C., reaction time should be kept at an empirically determined minimum to avoid unnecessary decomposition of the dinitrogen complexes. Progress of the reaction can be followed spectroscopically by IR or NMR, with phosphorus NMR being particularly useful. Once the minimum essential reaction time is determined in this way, it will remain constant as long as reaction conditions are not changed.

Dihydrogen or dinitrogen ligands in the complexes such as $RuH_2(H_2)_2(PR_3)_2$, $RuH_2(H_2)(N_2)(PR_3)_2$, $RuH_2(N_2)_2(PR_3)_2$, $RuH_2(H_2)(PR_3)_3$ and $RuH_2(N_2)(PR_3)_3$ can be displaced by other electron pair donor ligands to yield other complexes. Examples of such electron pair donors particularly relevant to the current invention comprise dihydrogen, dinitrogen, and nitriles which are some of the organic reactants, intermediates, products, and solvents of hydrogenation reactions of the present invention. Alcohols, amines, imines, and aldehydes are also useful electron pair donors. For complexes such as $RuH_2(H_2)_2(PR_3)_2$ and $RuH_2(N_2)_2(R_3)_2$, either one or both of the dihydrogen or dinitrogen ligands can be displaced by added electron pair donors to form other ruthenium complexes with amine, alcohol, imine, ether, nitrile, ester, amide, alkene, alkyne, ketone or aldehyde ligands. In some cases, mixtures of the ruthenium complexes may be obatined incorporating two or more different electron pair donor ligands. It is not necessary to purify such mixtures; they can be used directly in hydrogenation reactions. For example, the complex formed when the added electron pair donor ligands are nitriles, hereafter referred to as "nitrile complexes," need not be purified before use in hydrogenations. NMR and IR spectra of nitrile complexes typically indicate the presence of hydride, phosphine, dinitrogen, and nitrile ligands. Nitrile complexes can be preformed or can form in situ on mixing catalyst with nitriles in a hydrogenation reaction.

Solvents which are usable in the preparation of the complex comprise those described above for preparation of dinitrogen complexes as well as the added ligand itself provided it is a liquid at the reaction temperature and is capable of dissolving the reactants sufficiently for reaction to take place.

Temperature, pressure, and agitation requirements are as described above for preparation of dinitrogen complexes. The preferred temperature and pressure are ambient, i. e., about 15° C. to about 25° C. and 1 atmosphere. It is not necessary for the reactants to be completely dissolved for reaction to occur. As long as there is some solubility and sufficient agitation, the reaction will take place. Normally ligand exchange is rapid, complete within minutes after mixing. The product complexes can be isolated by removal of solvent and filtration, or may be used without isolation.

If the reaction mixture is allowed to remain in contact beyond the time required for ligand exchange, and especially when temperatures above ambient are employed, secondary reactions can occur. For example, in the presence of hydrogen, nitrile complexes can be partially hydrogenated to imine complexes. The necessary hydrogen can be added intentionally, or can be that hydrogen released by ligand exchange of a dihydrogen complex. Alternatively, when amines are used in ligand exchange to prepare amine complexes, the amine complex can be dehydrogenated to an imine complex. Such imine complexes are themselves useful catalysts. These secondary hydrogenation and dehydrogenation processes can result in mixtures of various nitrile, imine, and amine complexes which can be used without purification in hydrogenation reactions.

The complexes with the electron pair donor ligand described above may be more stable under certain conditions than the dihydrogen complexes from which they can be derived. This increased stability facilitates catalyst storage and recycle.

The ruthenium complexes of the present invention have utility as catalysts. They are useful in catalytic hydrogenation reactions, for example, in the reduction of olefins, in the reduction of nitro compounds to amines and, especially, in the reduction of nitriles, which are generally difficult to hydrogenate catalytically, to amines. The most important commercial use of these catalysts is thought to be in the reduction of adiponitrile to either 6-aminohexanenitrile or to hexamethylene diamine or to mixtures of the two.

There are no reported examples of compounds of Class IV with simple monodentate L. Complexes with the apparent stoichiometry $RuH_2L^1{}_3(PR_3)$, can be formed in organic solvents. The molar ratio of $PR_3$ to ruthenium compound can range from 1 to <2 moles of $PR_3$ to 1 mole of ruthenium compound. Preferably, only one equivalent of $PR_3$ is provided per equivalent of ruthenium compound. These Class IV complexes display even greater hydrogenation activity than ruthenium complexes of Class I–III. In aromatic solvents, the arene complexes, $(arene)RuH_2(PR_3)$, can form, but such arene complexes have lower activity for hydrogenation reactions than the complexes of the present invention prepared in non-aromatic solvents, and are not preferred. These are no reported examples of $RuH_2(PR_3)L_3$ with simple monodentate L, probably because such complexes are very labile and difficult to isolate, purify, and characterize. An advantage of the present invention is that isolation and purification are not necessary. The ruthenium complexes of Class IV or formula II can be prepared and used as catalysts in situ.

There are no generally applicable methods of preparing monomeric ruthenium complexes such as $RuX_2(PR_3)_3$, $RuHX(PR_3)_3$, and $RuX_2(PR_3)_4$. The specific ruthenium complex or complexes of formula I or II formed by the process of the current invention, depends on choice of $PR_3$, L or $L^1$, and reaction conditions such as the $PR_3$/Ru ratio employed. In some cases, a single ruthenium complex can predominate. In other cases, a mixture of ruthenium complexes can be obtained with varying L. Generally, it is not necessary to cleanly produce a single ruthenium complex since mixtures of complexes are also very useful for hydrogenation reactions. The primary advantage of the present invention is that such catalysts need not be isolated, but can be formed and used in situ for hydrogenation reactions.

The particular class of ruthenium complex produced by the current invention depends, to a large extent, on the steric bulk of the phosphorus ligands(s) employed. The concept of cone angle, described by C. A. Tolman in *Chemical Reviews*, 1977, Vol. 77, pp. 313–348, is a valuable tool for classifying $PR_3$ ligands and understanding how their steric bulk determines which class of complex is obtained. Small ligands, with cone angles of about 130° or less, such as the tri-n- alkylphosphines, including for example tributylphosphine, favor formation of complexes of Class I. Intermediate size ligands, with cone angles of 140°–150°, favor formation of complexes of Class II. Large ligands, with cone angles of 160°–180°, favor formation of complexes of Class III.

Since each R substituent group on $PR_3$ can be varied independently, the steric bulk of $PR_3$ can be varied continuously over a wide range. Since steric size can be continuously varied, the boundaries between classes of ruthenium complexes are not sharply delineated. As a consequence, in the process of the present invention for cases where complexes of Class II can be produced, mixtures are often obtained comprising, in addition, some complexes of Class I or Class III. In such cases, the exact composition of the mixture obtained can be controlled, to some extent, by adjusting the molar ratio of organophosphorus ligand to ruthenium compound used in the preparation. For example, where mixtures of Class I and Class II complexes are obtained, formation of Class I complexes can be favored by using a large excess of organophosphorus ligand in the preparation while formation of Class II complexes can be favored by using only three $PR_3$ per ruthenium compound, i.e., little or no excess of ligand. Similar considerations apply to controlling mixtures of Class II, III, and IV complexes. Complexes of Class III can be favored by using only two $PR_3$ per ruthenium while those of Class II can be favored by using three or more $PR_3$ per ruthenium. Complexes of Class II, III, and IV are preferred for hydrogenation reactions. Complexes of Classes III and IV are especially preferred, and especially those with large phosphorus ligands which substantially prevent formation of complexes of Class II even in the present of excess organophosphorous ligand. Complexes of class III where $PR_3$ is $PCy_3$ are most preferred because they are generally more stable than complexes of Class IV.

Each class of ruthenium complex, i.e., $RuH_2(PR_3)_4$, $RuH_2(H_2)(PR_3)_3$, or $RuH_2(H_2)_2(PR_3)_2$, has a distinctive NMR pattern, based on symmetry of the complex. For example, with octahedral geometry around Ru, cis-$RuH_2(PR_3)_4$ contains two different types of $PR_3$ ligands: two equivalent $PR_3$ each of which is trans to a H ligand and two equivalent $PR_3$ trans to each other. This leads to a phosphorus NMR spectrum described as an $A_2X_2$ pattern which is understood by one skilled in the art as resulting in a pair of triplets of equal intensity. A complex, but distinctive, multiplet is observed for the hydride signal in the proton NMR and integration should be correct for four $PR_3$ ligands and two hydride H.

$RuH_2(H_2)(PR_3)_3$ typically show only single lines in both the proton and phosphorus NMR due to rapid ligand and H2-hydride exchange, but integration of the proton NMR should be correct for four hydrides and 3 $PR_3$ ligands. One valuable diagnostic for identifying $RuH_2(H_2)(PR_3)_3$ species is their tendency to rapidly exchange $H_2$ for $N_2$ under a dinitrogen atmosphere forming $RuH_2(N_2)(PR_3)_3$, which has a more distinctive NMR signature. The phosphorus NMR shows a $A_2X$ pattern, i.e., a triplet of intensity one and a doublet of intensity two. The proton NMR spectrum comprises a distinctive pair of complex multiplets of equal intensities indicating two non-equivalent hydrides, such as would be expected for an octahedral geometry with one hydride trans to a $PR_3$ ligand and the other trans to a $N_2$ ligand. $RuH_2(H_2)(PR_3)_3$ can be easily recognized by comparing proton and phosphorus NMR spectra of a solution prepared under $H_2$ to a solution prepared under N2.

Finally, $RUH_2(H_2)_2(PR_3)_2$ show a single line phosphorus NMR spectrum. Under high resolution conditions, the hydride signal in the proton NMR spectrum appears as a triplet due to coupling to two equivalent $PR_3$ ligands, and the relative intensities of the hydride and ligand protons integrate correctly for a ratio of six hydrides and 2 $PR_3$ ligands. $RuH_2(H_2)_2(PR_3)_2$ can also be distinguished by their tendency to exchange $H_2$ for $N_2$ to form $RuH_2(N_2)_2(PR_3)_2$. These dinitrogen complexes display a single line in their proton-decoupled phosphorus NMR which becomes a triplet with proton coupling, confirming the presence of two hydrides. The hydride signal in the proton NMR appears as a triplet with coupling to two equivalent PR3 phosphorus nuclei. Formation of $RuH_2(H_2)_2(PR_2)_2$ can be provided by its reaction with nitrogen forming $RuH_2(N_2)_2)PR_3)_2$ which can be established by comparing proton and phosphorus NMR spectra of a solution prepared under $H_2$ to a solution prepared under $N_2$.

The new ruthenium complexes, $RuH_2L^1{}_3(PR_3)$, were not characterized by NMR. They were prepared and used in situ for hydrogenation reactions.

This invention provides a catalyst, comprising at least one ruthenium complex of formula II

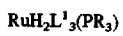

$$RuH_2L^1{}_3(PR_3) \qquad \text{II}$$

wherein $PR_3$ is an organophosphorus ligand; each R is a substituent independently selected from the group consisting of H, R', OR', $OSiR'_3$, $NH_2$, NHR' and $NR'_2$; each R' is independently selected from the group consisting of a hydrocarbyl group, and an assembly of at least two hydrocarbyl groups connected by ether or amine linkages; and each $L^1$ is a neutral electron pair donor ligand selected from the group consisting of $H_2$, $N_2$, nitriles, amines, alcohols, esters, ethers, amines, alkenes, alkynes, aldehydes, ketones, and imines. The definition and examples of a hydrocarbyl group and an organophosphorus ligand are the same as for formula I. Suitable 2-electron donor L ligands, which are well known to those skilled in the art, are described in Principles and Applications of Organotransition Metal Chemistry by J. P. Collman et al., University Science Books, Mill Valley, Calif. (1987), chapters 2 and 3. The preferred $L^1$ are molecules containing fully saturated Lewis basic donors comprising amines, alcohols, and ethers. Less preferred $L^1$ are molecules containing unsaturated, potentially hydrogenatable Lewis base donors comprising alkenes, alkynes, aldehydes, ketones, nitriles, imines, and esters. These can be used, but can be partially or completely hydrogenated in the course of preparing the ruthenium complex according to the current invention or while the complex is subsequently used in a hydrogenation reaction. $L^1$ ligands can be aliphatic, aromatic, or alkylaromatic in nature and can be substituted with non-interfering functional groups including the Lewis base functional groups listed above. Examples of suitable $L^1$ comprise amines such as butylamine and hexamethylenediamine, ethers such as tetrahydrofuran and t-butyl methyl ether, nitriles such as butyronitrile or adiponitile, esters such as ethyl acetate or dimethyl adipate, and amides such as N,N-dimethylacetamide. Preferred $L^1$ comprise amines and ethers. Most preferred $L^1$ comprise the hydrogenation product formed from the hydrogenation substrate; for example, in the case of an adiponitrile hydrogenation, hexamethylenediamine would be a most preferred $L^1$.

The catalyst comprising at least one ruthenium complex of formula II is prepared by a process similar to that for the preparation of the ruthenium complexes of formula I. One difference is that to the ruthenium starting material, as defined above for formula I, $PR_3$, gaseous hydrogen and organic solvent, an amount of $L^1$ is added. For the present process the mole ratio of $PR_3$ to ruthenium compound is at least 1 but less than 2 moles per one mole of ruthenium compound. The preferred mole ratio of $PR_3$:Ru is 1:1. The amount of $L^1$ used can vary over a wide range and depends partly on the nature of $L^1$ and how strongly $L^1$ coordinates to ruthenium. The $L^1$:Ru mole ratio employed can vary from about 3:1 to as much as 10000:1 or even higher. Since most $L^1$ bind weakly to ruthenium and do not interfere with hydrogenation, very high $L^1$:Ru ratios can be often used.

Solvents which can be employed are as described above for ruthenium complexes of formula I, except that solvents containing aromatic structures are generally not preferred because they can react with the catalyst forming arene complexes, which are less active in hydrogenation reactions than the catalysts formed in non-aromatic solvents. Especially preferred solvents comprise the $L^1$ ligands themselves, with $L^1$:Ru ratios of from about 1000:1 to about 5000:1. Temperature, pressure, and agitation requirements are as described above for ruthenium complexes of formula I. When more than one $L^1$ ligand is present in the above process, mixtures of ruthenium complexes of formula II incorporating various combinations of the different $L^1$ ligands can be formed. Further, ruthenium complexes of formula II are generally less stable than those of Classes I–III. An advantage of the current invention is that solutions obtained by the proceeding process can be used in hydrogenation reactions without further treatment, i.e., without isolation or purification of any ruthenium complex or mixture of complexes.

The ruthenium complexes of formula I and formula II have utility as catalysts. They are useful in catalytic hydrogenation reactions, for example in the reduction of alkenes to alkanes, in the reduction of nitro compounds to amines and, especially, in the reduction of nitriles, which are generally difficult to hydrogenate catalytically, to amines. The most important commercial use of these catalysts is thought to be in the reduction of adiponitrile to either 6-aminohexane-nitrile or to hexamethylenediamine or to mixtures of these two compounds.

The present invention further provides a process for the hydrogenation of an organic nitrile comprising contacting the nitrile with gaseous hydrogen in the presence of a catalyst, comprising at least one ruthenium complex of formula II, as described above. The nitrile, hydrogen and catalyst are subsequently agitated to form a primary amine. The present invention also provides an in situ process for the hydrogenation of an organic nitrile wherein the nitrile is added to the ruthenium complex catalyst preparation comprising the ruthenium compound $R^2{}_2RuA_2$, organophosphorus ligand, at least one $L^1$ ligand, gaseous hydrogen and the organic solvent, thus allowing for ruthenium complex catalyst formation and nitrile hydrogenation all in one step.

Suitable nitrile substrates which are applicable to these hydrogenation processes of the present invention comprise those having at least one CN group which is capable of being hydrogenated to the corresponding primary amine. Typically, the nitrile substrate is a monomeric material with one or two CN groups. However, the nitrile substrate can also be oligo- or polymeric, with either regularly occurring or occasional CN functional groups, comprising, for example, fluoronitriles such as $F(CF_2C_2)_nCH_2CH_2CN$ wherein n ranges from 2 to about 6. Complete reduction of a dinitrile to a diamine is one embodiment of the present hydrogenation processes.

Suitable nitrile substrates comprise the classes of linear or branched saturated aliphatic $C_2$–$C_{18}$ mono- and $C_3$–$C_{19}$ dinitriles and phenyl derivatives thereof, $C_4$–$C_{13}$ saturated alicyclic mono- and $C_5$–$C_{14}$ dinitriles, $C_3$–$C_{18}$ linear or branched olefinically unsaturated aliphatic nitriles, $C_6$–$C_{13}$ olefinically unsaturated alicyclic nitriles, $C_7$–$C_{14}$ aromatic mono- and dinitriles, $C_{6-C8}$ heterocyclic nitrogen and oxygen mononitriles, $C_3$–$C_4$ cyanoalkanoic amides, $C_2$–$C_{12}$ saturated aliphatic cyanohydrins or hydroxynitriles, or mixtures of the above-described nitriles, wherein said nitriles can also contain non-interfering substituents.

Examples of some substituents which generally do not interfere with the desired hydrogenation reaction comprise hydroxyl, amine, ether, alkyl, alkoxy, and aryloxy. For sample, cyanohydrins and hydroxynitriles are both acceptable nitriles. Unsaturated, hydrogenatable substituents such as ester, amide, aldehyde, imine, nitro, alkene, and alkyne are permissible in that they do not interfere with hydrogenation of the nitrile group, but they may themselves be hydrogenated partly or completely in the course of the nitrile hydrogenation. For example, 2-pentenenitrile can be hydrogenated completely to aminopentane. Carboxylic acids are generally not acceptable substituents since they react with the catalyst, deactivating it.

Representative examples of specific nitriles applicable in the invention process comprise: acetonitrile ($C_2$), propionitrile ($C_3$), butyronitrile ($C_4$), valeronitrile ($C_5$), capronitrile ($C_6$), 2,2-dimethylpropanenitrile, enanthonitrile ($C_7$), caprylonitrile ($C_8$), pelargononitrile ($C_9$), caprinitrile ($C_{10}$), hendecanenitrile ($C_{11}$), lauronitrile ($C_{12}$) tridecanenitrile ($C_{13}$), myristonitrile ($C_{14}$), pentadecanenitrile ($C_{15}$), palmitonitrile ($C_{16}$), margaronitrile ($C_{17}$), stearonitrile ($C_{18}$), phenylacetonitrile (benzyl nitrile), napthylacetonitrile, malononitrile, succinonitrile, glutaronitrile, 2-methylglutaronitrile, adiponitrile, acrylonitrile, methacrylonitrile, 2-methyleneglutaronitrile, 1,4-dicyano-2-butene, 1,4-cyano-1-butene, dodecanedinitrile, 3-butenenitrile, 4-pentenenitrile, 3-pentenenitrile, 2-pentenenitrile, 2-hexenenitrile, 2-heptenenitrile, glycolonitrile (formaldehyde cyanohydrin), hydracrylonitrile (ethylene cyanohydrin), eqicyanohydrin (gamma-cyanopropylene oxide), lactonitrile, pyruvonitrile, cyclohexanecarbonitrile, benzonitrile, o-tolylnitrile, m-tolylnitrile, p-tolylnitrile, anthranilonitrile, m-aminobenzonitrile, p-aminobenzonitrile, 1-napthonitrile, 2-napthonitrile, phthalonitrile, isophthalonitrile, terephthalonitrile, mandelonitrile, 2-pyridmenitile, 3-pyridinenitrile, 4-pyridinenitrile, or 2-furylacetonitrile.

Preferred nitriles in the process are adiponitrile, 2-methylglutaronitrile, and dodecanedinitrile.

The present hydrogenation processes can be conducted in the neat state, i.e., no solvent, provided that the nitrile and product amine are liquids at the reaction temperature employed and that the catalyst is sufficiently soluble therein However, use of a solvent is preferred to facilitate contacting of the reactants and removal of heat. The solubility of the respective materials in the solvent (or mixture of solvents) should be significantly large enough to initiate and maintain the hydrogenation process.

Solvents which are usable in these hydrogenation processes must be inert toward hydrogenation under the reaction conditions and possess adequate solvating ability for the substrate nitrile and catalyst.

Although the solvent employed is normally and preferably anhydrous, this is not a strict requirement. While the amount of water present is normally, and preferably, less than about 0.01 mole of water per mole of nitrile, larger amounts of water, up to about 0.1 to about 1 mole of water per mole of nitrile, generally do not produce significant amounts of alcohol by-products. In the case of a hydrophobic nitrile and hydrophobic solvent, large amounts of water, even a second liquid phase, can be present and do not interfere with normal hydrogenation. Suitable solvents comprise $C_6$–$C_{12}$ non-fused benzenoid hydrocarbons and $C_1$–$C_{18}$ alkyl derivatives thereof, $C_5$–$C_{30}$ linear or branched saturated aliphatic or alicyclic hydrocarbons, $C_2$–$C_{12}$ aliphatic ethers, $C_4$–$C_{12}$ saturated aliphatic cyclic mono- or diethers, or $C_7$–$C_{14}$ aromatic ethers, or mixtures thereof By the term "non-fused benzenoid hydrocarbons" is meant that if more than one benzene ring is present in the hydrocarbon, the rings are isolated and not fused together. Thus, the term encompasses biphenyl, but not naphthalene.

Suitable solvents further comprise amines, especially those amines produced by hydrogenation of the above nitriles which are liquid at reaction temperature. Representative examples of specific useful solvents comprise ammonia, methylamine, ethylamine, n-propylamine, isopropylamine, n-butylamine, amylamine, azacycloheptane, 2-methyl-pentamethylenediamine and hexamethylene-diamine, xylene, hexamethylbenzene, biphenyl, n-octadecylbenzene, benzene, toluene, pentane, cyclopentane, cyclohexane, methylcyclohexane, hexane, isoctane, decane, cyclodecane, tetrahydrofuran, p-dioxane, 2,5-dimethyltetrahydrofuran, methyl tetrahydrofurfuryl ether, dimethyl ether, 1,2-dimethoxyethane, diglyme, diethylether, diisopropyl ether, anisole, diphenylether, and mixtures thereof.

Preferred solvents comprise ammonia, THF, t-butyl methyl ether, toluene, n-amylamine, n-butylamine, 2-methyl-pentamethylenediamine, and hexamethylenediamine. Most preferred, when the amine product of the hydrogenation is a liquid at reaction temperature, is to use that same amine product as the reaction solvent. For example, butylamine can be used as the solvent when hydrogenating butyronitrile or hexamethylenediamine can be used as the solvent when hydrogenating adiponitrile.

The amount of catalyst used can vary from about 10 mole percent, based on nitrile to be hydrogenated, to about 0.01 mole percent. The preferred amount of catalyst is between about 1% and about 0.1% of the amount of nitrile to be hydrogenated on a molar basis. Larger or smaller amounts of catalyst can be used at the expense of catalyst cost or reaction time respectively.

Excess organophosphorous ligand can be present if desired and does not interfere with hydrogenation. Although excess organophosphorous ligand is not required, the presence of excess organophosphorous ligand ensures that there is always adequate organophosphorous ligand to stabilize the ruthenium catalyst, even if adventitious oxygen oxidizes a small amount of organophosphorous ligand to the corresponding ligand oxidation product, e.g., a phosphine oxide, or other side reactions degrade portions of the organophosphorous ligand. Ligand oxidation products formed in this manner can also be present and do not interfere with hydrogenation reactions. The molar ratio of excess organophosphorous ligand to ruthenium may vary from zero to about 60 or even more. The preferred molar ratio is between zero and about 30, with a molar ration of about 2 to about 25 being most preferred.

The hydrogenation can be conducted at any convenient temperature, from about 0° C. to about 200° C. Lower temperatures require prolonged reaction times while higher temperatures reduce catalyst life and reduce the yield of the desired primary amine products. The preferred temperature is in the range of about 60° to about 120° C., with about 80° to about 100° C. being most preferred.

The source of hydrogen can be hydrogen gas or mixtures of hydrogen gas with other gases which do not interfere with the desired hydrogenation. Non-interfering gases comprise, for example, inert gases, such as helium, argon, and nitrogen. Oxygen and carbon monoxide should be avoided since they can react with the catalysts.

The pressure employed can be from about 100 kPa (1 atmosphere) to about 15000 kPa or even higher. Elevated pressures are preferred since the solubility of hydrogen is increased which leads to higher reaction rates. However, pressures above about 7000 kPa to about 10000 kPa are generally avoided due to the high cost of equipment capable of operating at such pressures. The preferred pressure is in the range of about 3550 kPa to about 10000 kPa. Pressures between about 5000 kPa and about 7000 kPa are most preferred.

The hydrogenation of nitriles is a two-phase reaction. Therefore, it is essential to provide adequate gas-liquid contact to enable the gaseous hydrogen to dissolve in the liquid reaction phase. Adequate gas-liquid contact can be facilitated by any of the various agitation methods familiar to those skilled in the art. Typical methods comprise sparging gas below the liquid surface in a tank reactor, stirring the liquid in a tank reactor to draw gas into the liquid and create bubbles, use of packing in a tower reactor to obtain high liquid surface area, or use of a bubble column reactor, wherein bubbles of gas are introduced into the reactor and rise through the liquid phase.

The catalyst comprising at least one ruthenium complex of formula I is also useful in a selective hydrogenation process wherein a dinitrile is partially hydrogenated to yield an aminonitrile comprising contacting the dinitrile with gaseous hydrogen in the presence of the catalyst comprising at least one complex of formula II, and subsequently agitating the dinitrile, hydrogen and catalyst for an amount of time selected to favor yield of the aminonitrile over yield of a diamine. For example, the major intermediate in adiponitrile hydrogenation, 6-aminocapronitrile, can be prepared in high yield if the hydrogenation is stopped at an intermediate stage. This aminonitrile can then be directly hydrolyzed and polymerized to Nylon 6. The present invention also provides an in situ process for the selective hydrogenation process wherein the dinitrile is added to the ruthenium complex catalyst preparation comprising the ruthenium compound $R^2{}_2RuA_2$, organophosphorus $PR_3$ ligand, at least one $L^1$ ligand, gaseous hydrogen, and the organic solvent, thus allowing for the catalyst formation and selective hydrogenation all in one step.

The dinitrile used in these selective hydrogenation processes can be any aliphatic dinitrile comprising about 3 to about 14 carbon atoms, but preferably comprising about 6 to about 12 carbon atoms. Preferably, the carbon atoms are arranged in a linear or branched chain. Especially preferred examples of dinitriles and their product comprise adiponitrile hydrogenated to 6-aminocapronitrile, 2-methylglutaronitrile hydrogenated to a mixture of two isomeric aminonitriles (5-amino-2-methyl valeronitrile and 5-amino-4methyl valeronitrile), and dodecanedinitrile hydrogenated to 12-aminododecanenitrile.

The amount of catalyst excess organophosphorous ligand, solvents, temperature, pressure, agitation requirements and sources of hydrogen are the same as discussed above for the hydrogenation of nitriles to primary amines.

The desired product of the selective reduction, an aminonitrile, is an intermediate in one embodiment of the present hydrogenation process which eventually results in the formation of a diamine. The aminonitrile concentration in the reacting mixture passes through a maximum as the reaction progresses. One objective of this embodiment of the present invention is to maximize the concentration of the aminonitrile in the reacting mixture at the highest possible conversion of the starting dinitrile. The yield of the aminonitrile and the position of the maximum with respect to dinitrile conversion depend on operating conditions such as temperature, hydrogen pressure, amount and kind of catalyst, dilution of starting dinitrile, as well as, the type of solvent. These variables in turn influence the optimum contact time for the reaction. Conventional nitrile hydrogenation catalysts frequently give aminocapronitrile (ACN) selectivities approximating those expected statistically, assuming the two ends of the dinitrile are hydrogenated independently and at comparable rates. In contrast, the catalysts of the present invention give aminonitrile selectivities higher than those expected statistically.

The optimum reaction time of the present invention needed to favor formation of an aminonitrile need be determined only once for any given set of reaction conditions. Once the optimum has been determined, it will remain constant as long as reaction conditions, such as catalyst, reactant concentrations, temperature, and pressure are held constant.

Abbreviations used throughout are:
ACN aminocapronitrile
ADN adiponitrile
CPI 2-cyano cyclopentylimine
DMF N,N-dimethyl formamide
Dytek A® 2-methyl-pentamethylene diamine
Et ethyl
HMD hexamethylenediamine
HMI hexamethyleneimine (aka azacycloheptane)
Me methyl
MGN 2-methylglutaronitrile
MTBE methyl t-butyl ether
$Bu^i$ isobutyl
$Bu^n$ n-butyl
COD cyclooctadiene
COT cyclooctatriene
d doublet
L any neutral 2-electron donor ligand (including $H_2$, $N_2$, phosphines, etc.)
m medium intensity IR band or multiplet NMR lines
N112 aminocapronitrile
P triorganophosphine (e.g. triphenylphosphine)
Ph phenyl
$Pr^i$ isopropyl
q quartet
s strong intensity IR band or singlet NMR line
t triplet
THA tetrahydroazapine
THF tetrahydrofuran
w weak intensity IR band
Definitions
Yield: moles of product formed/moles of reactant charged x 100%
Selectivity: moles of product formed/moles of reactant consumed x 100%

EXAMPLE 1

Preparation of $RuH_2(H_2)_2(PCy_3)_2$ and $RuH_2(N_2)_2(PCy_3)_2$

A solution of 0.0584 g (0.18 mmol) (COD)Ru(2-methylallyl)$_2$ and 0.1159 g (0.41 mmol) tricyclohexylphosphine in 5 ml tetrahydrofuran was heated to 70° C. under 860 kPa $H_2$. After 1.3 hours, the reaction was cooled and brought into a $N_2$-atmosphere glovebox. $^{31}P$ nmr of a sample prepared under nitrogen showed the product to be a mixture containing predominantly $RuH_2(H_2)_2(PCy_3)_2$ and the related dinitrogen complexes formed from it via reaction with the nitrogen atmosphere (e.g., $RuH_2(N_2)_2(PCy_3)_2$). Evaporation of a solution using a stream of nitrogen completely converted the dihydrogen complex to $RuH_2(N_2)_2(PCy_3)_2$, as shown by $^{31}P$ and $^1H$ nmr.

EXAMPLE 2

A. Preparation of ($h^6$-toluene)$RuH_2(PCy_3)$ in Toluene Solvent

A solution of 0.034 g (0.1 mmol) (COD)Ru(2-methylallyl)$_2$ and 0.056 g $PCy_3$ (0.2 mmol, 2P/Ru) in 5 ml toluene was heated in a Fisher-Porter tube at 70° C. under 860 kPa $H_2$. After 2 hours, the reaction was cooled and brought into the glovebox. The product was isolated by removal of solvent in vacuo. 31P and $^1H$ nmr identified the product as ($h^6$-toluene)$RuH_2(PCy_3)$. No $RuH_2(H_2)_2(PCy_3)_2$ or $RuH_2(N_2)_2(PCy_3)_2$ was detected. $^{31}P\{^1H\}$: 78.96 ppm (s), becomes a triplet when $^1H$ coupling is allowed, $J_{PH}=$ 42.6 Hz, establishing that there are two hydride ligands present. $^1H$: 10.6 ppm (d, 2H, hydrides, $J_{PH}=$42.6 Hz, establishes presence of a single phosphine ligand), 5–5.25 (m, 5H, aromatic protons on coordinated toluene).

B. ADN Hydrogenation with ($h^6$-toluene)$RuH_2(PCy_3)$

A solution containing 0.08 mmol ($h^6$-toluene)$RuH_2(PCy_3)$ and 27.7 mmol ADN in 35 toluene was heated in a stirred autoclave at 60° C. under 7000 kPa $H_2$. After 23 hours, the ADN conversion had reached 32%.

For comparison, a mixture of 0.0704 g $RuH_2(H_2)_2(PCy_3)_2$ prepared as shown below (0.1 mmol) and 2.9154 g ADN (27 mmol, 270 ADN/Ru) in 35 ml toluene was heated in a stirred autoclave at 60° C. under 7000 kPa $H_2$. After 20.75 h, the composition was 15% ADN, 70% ACN, and 15% HMD. Thus ADN conversion had reached 85%, with selectivity to ACN of 82%.

Preparation of $RuH_2(H_2)_2(PCy_3)_2$ from (COD)$RuCl_2$

A mixture of 1.74 g Ru(COD)Cl$_2$ (6.2 mmol), 3.49 g $PCy_3$ (12.5 mmol), 2.14 g NaOH (54 mmol), 0.0579 g benzyl triethylammonium chloride (0.25 mmol, phase-transfer catalyst), 15 ml toluene, and 5 ml water was stirred under 7000 kPa hydrogen at 40° C. for 7.5 hours. After cooling under hydrogen, the reaction mixture was worked up in a nitrogen-filled glovebox. The solid product was isolated by filtration, washed with 10 ml heptane, and dried under a stream of nitrogen to give 4.0 g pale yellow powder (96% yield). The product was identified by comparison of its $^1H$ and $^{31}P$ nmr to literature data.

EXAMPLE 3

Preparation of PnBu$_3$ complexes in Toluene Solvent

A solution of 0.379 g (0.12 mmol) (COD)Ru(2-methylallyl)$_2$ and 0.0482 g (0.24 mmol) PhBu$_3$ in 5 g toluene was heated in a Fisher-Porter tube at 70° C. under 860 kPa $H_2$. After 1.7 hours, the reaction was cooled and brought into the glovebox. The solvent was removed in vacuo. $^{31}P$ and $^1H$ nmr showed the product to be a mixture of about 50% $RuH_2(H_2)(PnBu_3)_3$, $^1H$: −8.1 (br, s, hydrides). $^{31}P\{^1H\}$: 33.5 (s). 25% $RuH_2(N_2)(PnBu_3)_3$, 1H: −9.3 (dtd), −13.8 (m) both are hydrides. $^{31}P\{^1H\}$: 28.8 (d, 2P), 17.1 (t, 1P), $J_{PP}$−19.5 Hz, and 25% ($h^6$-toluene)$RuH_2(PnBu_3)$, $^1H$: −10.27 (d, hydrides, $J_{PH}$−45 Hz), 4.95–5.2 (m, $h^6$-toluene aromatic protons). $^{31}P\{^1H\}$: 46.3 (s).

EXAMPLE 4

In-situ catalyst preparation using PiPr$_3$, and ADN hydrogenation in n-butylamine solvent Examples 4A–4D, summarized in the following table, demonstrate that phosphine is required to generate an active and stable catalyst, but that excess phosphine reduces rate. They also demonstrate in situ catalyst generation and hydrogenation in n-butylamine solvent.

Summary of the Effect of P/Ru on ADN Hydrogenation Rate

| PiPr$_3$/Ru | Time for 50% ADN conversion | Relative rate |
|---|---|---|
| 0 | Catalyst deactivated (>>5 h) | very slow (<<0.1) |
| 1 | 0.5 h | 1.0 |
| 2.4 | 1 h | 0.5 |
| 6 | 1.5 h | 0.33 |

A. No Added Phosphine

A solution of 0.03048 g (COD)Ru(2-methylallyl)$_2$(0.095 mmol) and 0.9905 g ADN (9.163 mmol, 96 ADN/Ru) in 40 ml n-butylamine was heated in a stirred autoclave at 80° C. under 7000 kPa H$_2$. After 5 hours, the ADN conversion was less than 5%.

B. PiPr$_3$/Ru=1

A solution of 0.027 g (COD)Ru(2-methylallyl)$_2$ (0.084 mmol), 16 ul PiPr$_3$, (0.081 mmol, 0.96 P/Ru) and 1.08 g ADN (9.95 mmol, 119 ADN/Ru) in 35 ml n-butylamine was heated in a stirred autoclave at 80° C. under 7000 kPa H$_2$. After 4.2 hours, the ADN was completely hydrogenated and the yield of HMD was 92%.

C. PiPr$_3$/Ru=2.4

A solution of 0.0248 g (COD)Ru(2-methylallyl)$_2$ (0.077 mmol), 36 ul PiPr$_3$,(0.184 nnmol, 2.4 P/Ru) and 1.21 g ADN (11.2 mmol, 145 ADN/Ru) in 40 ml n-butylamine was heated in a stirred autoclave at 80° C. under 7000 kPa H$_2$. After 7 hours, the ADN was completely hydrogenated and the yield of HMD was 93%.

D. PiPr$_3$/Ru=6

A solution of 0.0256 g (COD)Ru(2-methylallyl)$_2$ (0.08 mmol), 94 ul PiPr$_3$, (0.48 mmol, 6 P/Ru) and 0.99 g ADN (9.2 mmol, 115 ADN/Ru) in 40 ml n-butylamine was heated in a stirred autoclave at 80° C. under 7000 kPa H$_2$. After 7.3 hours, 99% of the ADN was hydrogenated, yielding 46% ACN and 45% HMD.

EXAMPLE 5

In-situ catalyst preparation using PPh$_3$, and ADN hydrogenation in n-butylamine solvent A solution of 0.026 g (COD)Ru(2-methylallyl)$_2$ (0.08 mmol), 0.022 g PPh$_3$, (0.08 mmol, 1 P/Ru) and 0.87 g ADN (8 mmol, 100 ADN/Ru) in 35 ml n-butylamine was heated in a stirred autoclave at 80° C. under 7000 kPa H$_2$. After 8.5 hours, 96% of the ADN was hydrogenated, yielding 55% ACN and 31% HMD. Conversion of the intermediate ACN was incomplete.

EXAMPLE 6

Heterogenized Ru catalyst on silica-supported phosphine

A. Catalyst preparation

A silica-supported phosphine was prepared by grafting diphenyl-phosphopropyl silyl groups onto a commercially available silica support. The resulting material contained 0.4% P by weight. The silica support, a Grace-Davison 62 silica support, was dried at 400° C. in a stream of dry nitrogen overnight. The phosphine was attached to the surface by refluxing a 25% solution of 2-(diphenylphosphino)ethyl triethoxysilane in dry toluene overnight in the presence of the silica support. The modified support was washed with an excess of dry toluene and the product dried under vacuum. Then a mixture of (COD)Ru (2-methylallyl)$_2$ (0.028 g, 0.1 mmol) and the silica-supported phosphine (1.55 g, containing~0.2 mmol P) in 10 ml THF was heated in a Fisher-Porter tube at 70° C. under 860 kPa H$_2$ for 3 hours. Solvent removal in vacuo gave a brown powder.

B. Hydrogenation of 1,5-cyclooctadiene

An amount of the above catalyst estimated to contain 0.1 mmol Ru was combined with 10 mmol 1,5-cyclooctadiene in 15 g THF. The mixture was stirred in a Fisher-Porter tube at 20° C. under 860 kPa H$_2$ for 1.5 hours. Gas chromatographc analysis after 1.7 hours showed the presence of 28% COD, 46% cyclooctene, and 26% cyclooctane. After 5.7 hours, the mixture was completely hydrogenated to cyclooctane.

The catalyst was recovered by filtration and washed with several small portions of ether and THF. The recycled catalyst was found to be still active for 1,5-cyclooctadiene hydrogenation at 70° C. and 860 kPa H$_2$.

What is claimed is:

1. A process for the hydrogenation of an organic nitrile, comprising the steps of:
   (a) contacting the nitrile with gaseous hydrogen in the presence of a catalyst comprising at least one ruthenium complex of the formula, RuH$_2$L$^1$$_3$(PR$_3$) wherein PR$_3$ is an organophosphorus ligand;
      each R is a substituent independently selected from the group consisting of: H, R', OR', OSiR'$_3$, NH$_2$, NHR', and NR'$_2$;
      each R' is independently selected from the group consisting of: a hydrocarbyl group and an assembly of at least two hydrocarbyl groups connected by ether or amine linkages; and
      each L$^1$ is a neutral electron pair donor ligand selected from the group consisting of: H$_2$, N$_2$, nitriles, amines, alcohols, ethers, esters, amides, alkenes, alkynes, aldehydes, ketones and imines; and
   (b) subsequently agitating the nitrile, hydrogen and catalyst to form a primary amine.

2. The process of claim 1 wherein contact is made at a temperature of about 0° C. to about 200° C. at a pressure of about 100 kpa to about 15000 kPa, optionally in the presence of a solvent.

3. An in situ process for the hydrogenation of an organic nitrile, comprising the steps of:
   (a) contacting the nitrile with a ruthenium compound having the formula R$^2$$_2$RuA$_2$ wherein R$^2$ is a mono- or poly-, cyclic- or acyclic alkene ligand, present as either two separate ligands or as a single polyalkene ligand and A is an allyl ligand or a hydrocarbyl-substituted allyl ligand, the organophosphorus ligand PR$_3$, wherein the molar ratio of PR$_3$ to the ruthenium compound ranges from 1 to <2 moles of PR$_3$ to 1 mole of ruthenium compound, an organic solvent, and at least one L$^1$ ligand, with gaseous hydrogen at a temperature from about –30° C. to about 200° C.; and
   (b) subsequently agitating the solution to form a primary amine.

4. The process of claim 1 or 3 wherein the nitrile is selected from the group consisting of: adiponitrile, 2-methylgutaronitrile, 3-cyano-methyliso-butyrate, valeronitrile, and dodecanedinitrile.

5. The process of claim 1 or 3 wherein the nitrile is a dinitrile and the primary amine is a diamine.

6. The process of claim 1 or 3 wherein the catalyst $L^1$ ligand is selected from the group consisting of butylamine, hexamethylenediamine, tetrahydrofuran, t-butylmethylether, butyronitile, adiponitrile, ethylacetate, dimethyladipate, N,N-dimethylacetamide.

7. The process of claim 6 wherein the $L^1$ ligand is hexamethylene-diamine.

8. The process of claim 1 or 3 wherein all R substituents are the same and are selected from the group consisting of: a cyclohexyl group, an isopropyl group, and an n-butyl group.

9. A process for the selective hydrogenation of a dinitrile, comprising the steps of:
  (a) contacting said dinitrile with gaseous hydrogen in the presence of a catalyst comprising at least one ruthenium complex of the formula, $RuH_2L^1{}_3(PR_3)$ wherein $PR_3$ is an organophosphorus ligand;
    each R is a substituent independently selected from the group consisting of: H, R', OR', OSiR'$_3$, NH$_2$, NHR', and NR'$_2$;
    each R' is independently selected from the group consisting of a hydrocarbyl group, and a first hydrocarbyl group connected by an amine or an ether linkage to a second hydrocarbyl group; and
    each $L^1$ is a neutral electron pair donor ligand selected from the group consisting of: H$_2$, N$_2$, nitriles, amines, alcohols, ethers, esters, amides, alkenes, alkynes, aldehydes, ketones and imines; and
  (b) subsequently agitating the dinitrile, hydrogen and catalyst for an amount of time selected to favor yield of an aminonitrile over yield of a dimaine.

10. The process of claim 9 wherein contact is made at a temperature of about 0° C. to about 200° C. at a pressure of about 100 kPa to about 15000 kPa, optionally in the presence of a solvent.

11. An in situ process for the selective hydrogenation of a dinitrile, comprising the steps of:
  (a) contacting the dinitrile with a ruthenium compound having the formula $R^2{}_2RuA_2$ wherein $R^2$ is a mono- or poly-, cyclic- or acyclic alkene ligand, present as either two separate ligands or as a single polyalkene ligand and A is an allyl ligand or a hydrocarbyl-substituted allyl ligand, the organophosphorus ligand $PR_3$, wherein the molar ratio of $PR_3$ to the ruthenium compound ranges from 1 to <2 moles of $PR_3$ to 1 mole of ruthenium compound, an organic solvent and at least one $L^1$ ligand, with gaseous hydrogen at a temperature from about −30° C. to about 200° C.; and
  (b) subsequently agitating the solution for an amount of time selected to favor yield of an aminontrile over yield of a dimaine.

12. The process of claim 9 or 11 wherein the dinitrile is selected from the group consisting of: adiponitrile, 2-methylglutaronitrile and dodecanedinitrile.

13. The process of claim 9 or 11 wherein the catalyst L' ligand is selected from the group consisting of: butylamine, hexamethylenediamine, tetrahydrofuran, t-butylmethylether, butyronitrile, adiponitrile, ethylacetate, dimethyladipate, and N,N-dimethylacetamide.

14. The process of claim 13 wherein the $L^1$ ligand is hexamethylene-diamine.

15. The process of claim 9 or 11 wherein all R substituents are the same and are selected from the group consisting of: a cyclohexyl group, an isopropyl group, and an n-butyl group.

* * * * *